(12) United States Patent
Ansmann et al.

(10) Patent No.: US 7,083,780 B2
(45) Date of Patent: Aug. 1, 2006

(54) COSMETIC COMPOSITION CONTAINING HYDROXYETHERS

(75) Inventors: Achim Ansmann, Erkrath (DE); Rolf Kawa, Monheim (DE); Michael Neuss, Cologne (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 262 days.

(21) Appl. No.: 10/129,581

(22) PCT Filed: Nov. 29, 2000

(86) PCT No.: PCT/EP00/11938

§ 371 (c)(1),
(2), (4) Date: Dec. 4, 2002

(87) PCT Pub. No.: WO01/42180

PCT Pub. Date: Jun. 14, 2001

(65) Prior Publication Data
US 2003/0161847 A1 Aug. 28, 2003

(30) Foreign Application Priority Data
Dec. 11, 1999 (DE) ................ 199 59 917

(51) Int. Cl.
A61K 31/74 (2006.01)
A61K 7/42 (2006.01)
A61K 7/44 (2006.01)
A61K 7/00 (2006.01)

(52) U.S. Cl. ............ 424/78.02; 424/59; 424/60; 424/78.03; 424/78.08; 424/400; 424/401

(58) Field of Classification Search .......... 424/78.02, 424/78.08, 78.03, 59, 60, 400, 401
See application file for complete search history.

(56) References Cited

U.S. PATENT DOCUMENTS

| | | | |
|---|---|---|---|
| 4,172,887 A | 10/1979 | Vanlerberghe et al. | |
| 4,303,639 A | 12/1981 | Vanlerberghe et al. | |
| 4,832,868 A | 5/1989 | Schmid et al. | |
| 5,705,169 A | 1/1998 | Stein et al. | |
| 5,730,960 A | 3/1998 | Stein et al. | |
| 5,945,091 A | 8/1999 | Habeck et al. | |
| 6,193,960 B1 | 2/2001 | Metzger et al. | |
| 6,380,439 B1 | 4/2002 | Klaas et al. | |

FOREIGN PATENT DOCUMENTS

| | | |
|---|---|---|
| DE | 1 165 574 A | 8/1960 |
| DE | 2 024 051 A | 12/1971 |
| DE | 25 35 802 A1 | 2/1976 |
| DE | 197 12 033 A1 | 9/1998 |
| DE | 197 36 121 A1 | 10/1998 |
| DE | 197 56 377 A1 | 6/1999 |
| EP | 0 693 471 B1 | 1/1996 |
| EP | 0 694 521 B1 | 1/1998 |
| EP | 0 818 450 A1 | 1/1998 |
| EP | 1 060 740 A1 | 12/2000 |
| FR | 2 252 840 A | 8/1975 |
| GB | 962919 A | 7/1964 |
| GB | 1 333 475 A | 10/1973 |

OTHER PUBLICATIONS

Von U. Zeidler, "Uber das Spreiten von Lipiden auf der Haut", Fette-Seifen-Anstrichmittel, 87, (1985), pp. 403-408.

R. Lochhead et al., "Encyclopedia of Polymers and Thickeners for Cosmetics", Cosmetics & Toiletries, vol. 108, (May, 1993), pp. 95-114, 116-124, 127-130, 132-135.

C. Todd et al., "Volatile silicone fluids for cosmetic formulations", Cosmetics and Toiletries, vol. 91, (Jan., 1976), pp. 29-32.

P. Finkel, "Formulierung kosmetischer Sonnenschutzmittel", SÖFW-Journal, 122, (1996), pp. 543-546 & 548.

P. Finkel, "Formulierung kosmetischer Sonnenschutzmittel", Parfumerie und Kosmetik, 80, No. 3 (1999), pp. 10-12, 14-16.

"Kosmetische Färbemittel", Farbstoffkommission der Deutschen Forschungsgemeinschaft, Verlag Chemie, Weinheim, (1984), pp. 81-106.

*Primary Examiner*—Shelley A. Dodson
(74) *Attorney, Agent, or Firm*—Arthur G. Seifert; John F. Daniels

(57) ABSTRACT

The use of hydroxyethers obtainable by ring opening of olefinic oxides having 6 to 18 carbon atoms with alcohols having 1 to 18 carbon atoms andlor polyols having 2 to 18 carbon atoms and 2 to 10 hydroxyl groups or water are proposed as oil bodies in cosmetic and/or pharmaceutial preparations is described.

15 Claims, No Drawings

COSMETIC COMPOSITION CONTAINING HYDROXYETHERS

BACKGROUND OF THE INVENTION

The preparation of cosmetic or pharmaceutical compositions, for example creams, lotions or ointments, requires oil-soluble bases into which in many different lipid-soluble solids are present in dissolved form. A large number of natural and synthetic oils are suitable for this purpose, for example almond and avocado oil or ester oils based on short-chain triglycerides. The oil components in the compositions discussed also have a care action at the same time which is directly connected with skin fatting. Consumers want products which give a nonsticky, very rapidly occurring and longer-lasting feel of skin smoothness and suppleness and moreover are rich and exhibit good skin compatibilities.

The subjective sensation on the skin can be correlated and objectified using the physicochemical parameter of spreading of the oil bodies on the skin, as has been presented by U. Zeidler in Fette, Seifen, Anstrichmitt. 87, 403 (1985). According to this, cosmetic oil bodies can be divided into low-spreading (below 300 mm$^2$/10 min), medium spreading (about 300 to 1000 mm$^2$/10 min) and high-spreading oils (above 1000 mm$^2$/10 min). If a high-spreading oil is used as oil body in a pregiven formulation, then the desired feeling of skin smoothness is very rapidly achieved, although the result does not last for long. Conversely, if low-spreading oils are used, only a less marked feel of smoothness is achieved which remains virtually unchanged over a prolonged period and is therefore likewise unsatisfactory. The obvious combination of a low-spreading and a high-spreading oil surprisingly does not lead to the desired additive effect; instead, the strong smoothing action of the rapidly spreading oil component is perceived subjectively at the start, and then, quite independently, the effect of the slowly spreading oil. In practice, therefore, it is usually necessary to use complex mixtures of oil bodies matched exactly to one another which develop their action successively in the sense of a cascade without having a mutually negative influence. It is clear that the development of such systems is associated with high technical cost and is thus in need of improvement from an economical viewpoint as well.

Consequently, the object of the present invention was to provide novel compositions which have a nonsticky, very rapidly occurring and longer-lasting feel of skin smoothness and suppleness, are rich and have good skin compatibilities. Moreover, they should exhibit a good solution behavior for lipophilic solids.

BRIEF SUMMARY OF THE INVENTION

The present invention relates, in general, to the use of hydroxyethers obtainable by ring opening of olefinic oxides with alcohols and/or polyols or water as oil bodies in cosmetic and/or pharmaceutical preparations.

Surprisingly, it has been found that hydroxyethers obtainable by ring opening of olefin epoxides with alcohols and/or polyols or water are in a position to have improved sensory properties and are therefore suitable as oil bodies in cosmetic and/or pharmaceutical preparations. Moreover, they exhibit excellent dissolution properties for lipophilic solids, good skin compatibilities and improve the photostability of UV light protection filters to a considerable extent.

DETAILED DESCRIPTION OF THE INVENTION

Hydroxyethers (Epoxide Ring-Opening Products)

The hydroxyethers (ring-opening products) are known substances usually prepared by acid- or alkaline-catalyzed reaction of terminal or internal olefin epoxides with aliphatic alcohols. The hydroxyethers have the formula (I)

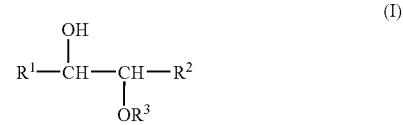

in which $R^1$ and $R^2$ are alkyl radicals having 4 to 16, preferably 8 to 12, carbon atoms, with the proviso that the sum of the carbon atoms of $R^1$ and $R^2$ is in the range from 4 to 16, preferably 6 to 10, and $R^3$ is an alkyl and/or alkenyl radical having 1 to 18 carbon atoms and/or the radical of a polyol having 2 to 18 carbon atoms and 2 to 10, preferably 4 to 6, hydroxyl groups. Typical examples are ring-opening products of α-hexene epoxide, α-octene epoxide, α-decene epoxide, α-dodecene epoxide, α-hexadecene epoxide, α-octadecene epoxide, i-hexene epoxide, i-octene epoxide, i-decene epoxide, i-dodecene epoxide, i-hexadecene epoxide and/or i-octadecene epoxide with alcohols having 1 to 18, preferably 1 to 8, carbon atoms, such as, for example, lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol and/or linolenyl alcohol. Preference is given to using ring-opening products of octene, decene and/or dodecene epoxides. In a particularly preferred embodiment of the invention, branched and cyclic alcohols having 1 to 18, preferably 1 to 8, carbon atoms can likewise be used.

Polyols which are suitable for the purposes of the invention preferably have 4 to 10 carbon atoms and at least two hydroxyl groups. Typical examples are glycerol;

alkylene glycols, such as, for example, ethylene glycol, diethylene glycol, propylene glycol, butylene glycol, hexylene glycol, and polyethylene glycols having an average molecular weight of from 100 to 1000 daltons;

technical-grade oligoglycerol mixtures having a degree of self-condensation of from 1.5 to 10, such as, for example, technical-grade diglycerol mixtures having a diglycerol content of from 40 to 50% by weight;

methylol compounds, such as, in particular, trimethylolethane, trimethylolpropane, trimethylol-butane, pentaerythritol and dipentaerythritol;

lower alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

aminosugars, such as, for example, glucamine.

The use amount of the hydroxyethers can be 1 to 60% by weight, preferably 2 to 50% by weight and in particular 3 to 10% by weight, based on the final concentration.

Lipophilic Solids

Lipophilic solids chosen from the group formed by UV light protection filters, bodying agents, waxes, fats, stabilizers, pearlescent waxes and/or partial glycerides can be present in dispersed form in the oil bodies according to the invention.

The term "UV light protection factors" means, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

- 3-benzylidenecamphor or 3-benzylidenenorcamphor and derivatives thereof, e.g. 3-(4-methylbenzylidene)-camphor, as described in EP 0693471 B1;
- 4-aminobenzoic acid derivatives, preferably 2-ethylhexyl 4-(dimethylamino)benzoate, 2-octyl 4-(di-methylamino)benzoate and amyl 4-(dimethylamino)-benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenyl-cinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methyl-benzophenone, 2,2'-dihydroxy-4-methoxybenzophenone;
- esters of benzalmalonic acid, preferably di-2-ethyl-hexyl 4-methoxybenzmalonate;
- triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);
- propane-1,3-diones, such as, for example, 1-(4-tert-butylphenyl)-3-(4'-methoxyphenyl)propane-1,3-dione;
- ketotricyclo(5.2.1.0)decane derivatives, as described in EP 0694521 B1.

Suitable water-soluble substances are:
- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and its salts;
- sulfonic acid derivatives of 3-benzylidenecamphor, such as, for example, 4-(2-oxo-3-bornylidenemethyl)-benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters can of course also be used in mixtures.

Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates.

Typical examples of fats are glycerides, i.e. solid or liquid (in this case often also referred to as oils) vegetable or animal products which consist essentially of mixed glycerol esters of higher fatty acids, and suitable waxes are inter alia natural waxes, such as, for example, candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithin and phospholipids. For the person skilled in the art, the term "lecithins" means those glycerophospholipids formed from fatty acids, glycerol, phosphoric acid and choline by esterification. In the specialist field, lecithins are therefore also often referred to as phosphatidylcholines (PC) and follow the general formula

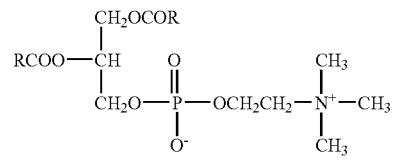

where R is typically a linear aliphatic hydrocarbon radical having 15 to 17 carbon atoms and up to 4 cis double bonds. Examples of natural lecithins which may be mentioned are cephalins, which are also referred to as phosphatidic acids and are derivatives of 1,2-diacyl-sn-glycerol-3-phosphoric acids. By contrast, the term "phospholipids" usually means mono- and, preferably, diesters of phosphoric acid with glycerol (glycerol phosphates) which are generally considered to be fats. In addition, sphingosines and sphingolipids are also suitable.

Stabilizers which can be used are metal salts of fatty acids, such as, for example, magnesium, aluminum and/or zinc stearate or ricinoleate.

Examples of suitable pearlescent waxes are: alkylene glycol esters, specifically, ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

The novel preparation of hydroxyethers and lipophilic fatty substances has the following composition—quantitative data based on the final concentration—:
 (a) 1 to 60% by weight, preferably 2 to 50% by weight and in particular 3 to 10% by weight, of hydroxyethers,
 (b) 0.1 to 30% by weight, preferably 0.5 to 10% by weight, of lipophilic solids, with the proviso that the quantitative data are made up to 100% by weight with water and further auxiliaries and additives.

Cosmetic and/or Pharmaceutical Preparations

The compositions according to the invention can be used for the preparation of cosmetic and/or pharmaceutical preparations, such as, for example, hair shampoos, hair lotions, foam baths, shower preparations, creams, gels, lotions, alcoholic and aqueous/alcoholic solutions, emulsions, wax/fatty compositions, stick preparations, powders or ointments. As further auxiliaries and additives, these compositions can also comprise mild surfactants, further oil bodies, emulsifiers, superfatting agents, thickeners (including polymers), silicone compounds, lecithins, phospholipids, biogenic active ingredients, deodorants, antiperspirants, antidandruff agents, film formers, swelling agents, antioxidants, hydrotropic agents, preservatives, insect repellants, self-tanning agents, tyrosine inhibitors (depigmentation agents), solubilizers, perfume oils, dyes and the like.

Typical examples of suitable mild, i.e. particularly skin-compatible, surfactants are monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylaminobetaines and/or protein-fatty acid condensates, the latter preferably being based on wheat proteins.

Suitable further oil bodies are, for example, Guerbet alcohols based on fatty alcohols having 6 to 18, preferably 8 to 10, carbon atoms, esters of linear $C_6$–$C_{22}$-fatty acids with liner $C_6$–$C_{22}$-fatty alcohols, esters of branched $C_6$–$C_{13}$-carboxylic acids with linear $C_6$–$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl, isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$–$C_{38}$-alkylhydroxycarboxylic acids with linear or branched $C_6$–$C_{22}$-fatty alcohols (cf. DE 19756377 A1), in particular dioctyl malate, esters of linear and/or branched fatty acids with polyhydric alcohols (such as, for example, propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$–$C_{22}$-fatty alcohol carbonates, Guerbet carbonates, esters of benzoic acid with linear and/or branched $C_6$–$C_{22}$-alcohols (e.g. Finsolv® TN), linear or branched, symmetrical or unsymmetrical dialkyl ethers having 6 to 22 carbon atoms per alkyl group, ring-opening products of epoxidized fatty acid esters with polyols, silicone oils (cyclomethicones, silicon methicone grades etc.) and/or aliphatic or naphthenic hydrocarbons, such as, for example squalane, squalene or dialkylcyclohexanes.

Suitable emulsifiers are, for example, nonionogenic surfactants from at least one of the following groups:
  addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;
  block copolymers, e.g. polyethylene glycol-30 dipolyhydroxystearates;
  alkyl and/or alkenyl oligoglycosides having 8 to 22 carbon atoms in the alk(en)yl radical and the ethoxylated analogs thereof;
  addition products of from 1 to 15 mol of ethylene oxide onto castor oil and/or hydrogenated castor oil;
  addition products of from 15 to 60 mol of ethylene oxide onto castor oil and/or hydrogenated castor oil;
  partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;
  partial esters of polyglycerol (average degree of self-condensation 2 to 8), polyethylene glycol (molecular weight 400 to 5000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;
  mixed esters of pentaerythritol, fatty acids, citric acid and fatty alcohol as in German patent 1165574 and/or mixed esters of fatty acids having 6 to 22 carbon atoms, methylglucose and polyols, preferably glycerol or polyglycerol,
  mono-, di- and trialkyl phosphates, and mono-, di- and/or tri-PEG alkyl phosphates and salts thereof;
  wool wax alcohols;
  polysiloxane-polyalkyl-polyether copolymers and corresponding derivatives;
  polyalkylene glycols, and
  Pemulen grades, e.g. Pemulen TR-1, Pemulen TR-2 (Goodrich).

The addition products of ethylene oxide and/or of propylene oxide onto fatty alcohols, fatty acids, alkylphenols or onto castor oil are known, commercially available products. These are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known from German patent 2024051 as refatting agents for cosmetic preparations.

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof.

Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term zwitterionic surfactants refers to those surface-active compounds which carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term ampholytic surfactants means those surface-active compounds which, apart from one $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine.

Finally, cationic surfactants are also suitable emulsifiers, those of the ester quat type, preferably methyl-quaternized difatty acid triethanolamine ester salts, being particularly preferred.

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, such as, for example, ethoxylated fatty acid glycerides, esters of fatty acids with polyols such as, for example, pentaerythritol or trimethylolpropane, fatty alcohol ethoxylates having a narrowed homolog distribution or alkyl oligoglucosides, and electrolytes such as sodium chloride and ammonium chloride.

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L /Grünau), quaternized wheat polypeptides, polyethyleneimine, cationic silicone polymers, such as, for example, amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in micro-crystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids, polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones. Further suitable polymers and thickeners are listed in Cosmetics & Toiletries Vol. 108, May 1993, page 95ff.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates. A detailed review of suitable volatile silicones can additionally be found in Todd et al., Cosm. Toil. 91, 27 (1976).

The term "biogenic active ingredients" means, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Cosmetic deodorants counteract, mask or eliminate body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents.

Suitable antimicrobial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monolaurate (GML), diglycerol monocaprate (DMC), salicylic acid N-alkylamides, such as, for example, n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf/Germany). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
nonionic emulsifiers,
coemulsifiers, bodying agents,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminum, zirconium or of zinc. Such suitable antihidrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine.

In addition, customary oil-soluble and water-soluble auxiliaries may be present in antiperspirants in relatively small amounts. Such oil-soluble auxiliaries may, for example, be:
anti-inflammatory, skin-protective or perfumed essential oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Antidandruff agents which may be used are Octopirox® (1-hydroxy-4-methyl-6-(2,4,4-trimethylpentyl)-2-(1H)-pyridone monoethanolamine salt), Baypival, piroctone olamine, Ketoconazol®, (4-acetyl-1-{4-[2-(2,4-dichlorophenyl)r-2-(1H-imidazol-1-ylmethyl)-1,3-dioxolan-o-4-yl-methoxyphenyl}piperazine, selenium disulfide, colloidal sulfur, sulfur polyethylene glycol sorbitan monooleate, sulfur ricinol polyethoxylate, sulfur tar distillates, salicylic acid (or in combination with hexachlorophene), undexylenic acid monoethanolamidesulfosuccinate Na salt, Lamepon® UD (protein undecylenic acid condensate), zinc pyrithione, aluminum pyrithione and magnesium pyrithione/dipyrithione magnesium sulfate.

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

As well as said soluble substances, insoluble light protection pigments, namely finely dispersed metal oxides or salts, are also suitable for this purpose. Examples of suitable metal oxides are, in particular, zinc oxide and titanium oxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, Titandioxid T 805 (Degussa) or Eusolex® T2000 (Merck). Suitable hydrophobic coating agents are here primarily silicones and, specifically in this case, trialkoxyoctylsilanes or simethicones. In sunscreens, preference is given to using micro- or nanopigments. Preference is given to using micronized zinc oxide. Further suitable UV light protection filters are given in the review by P. Finkel in SÖFW-Journal 122, 543 (1996) and Parfümerie und Kosmetik 3 (1999), page 11ff.

As well as the two abovementioned groups of primary light protection substances, it is also possible to use secondary light protection agents of the antioxidant type; these interrupt the photochemical reaction chain which is triggered when UV radiation penetrates the skin. Typical examples thereof are amino acids (e.g. glycine, histidine, tyrosine, tryptophan) and derivatives thereof, Imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

To improve the flow behavior, it is furthermore possible to use hydrotropic agents, such as, for example, ethanol, isopropyl alcohol or polyols. Polyols which are suitable here preferably have 2 to 15 carbon atoms and at least two hydroxyl groups. The polyols can also contain further functional groups, in particular amino groups, or can be modified with nitrogen. Typical examples are glycerol;

alkylene glycols, such as, for example, ethylene glycol, diethylene glycol, propylene glycol, butylene glycol, hexylene glycol, and polyethylene glycols having an average molecular weight of from 100 to 1000 daltons;

technical-grade oligoglycerol mixtures having a degree of self-condensation of from 1.5 to 10, such as, for example, technical-grade diglycerol mixtures having a diglycerol content of from 40 to 50% by weight;

methylol compounds, such as, in particular, trimethylolethane, trimethylolpropane, trimethylolbutane, pentaerythritol and dipentaerythritol;

lower alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

aminosugars, such as, for example, glucamine;

dialcoholamines, such as diethanolamine or 2-amino-1,3-propanediol.

Suitable preservatives are, for example, phenoxyethanol, formaldehyde solution, parabens, pentanediol or sorbic acid, and the other classes of substance listed in Annex 6, Part A and B of the Cosmetics Directive. Suitable insect repellants are N,N-diethyl-m-toluamide, 1,2-pentanediol or ethyl butylacetylaminopropionate, and a suitable self-tanning agent is dihydroxyacetone. Suitable tyrosine inhibitors, which prevent the formation of melanin and are used in depigmentation agents, are, for example, arbutin, kojic acid, coumaric acid and ascorbic acid (vitamin C).

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes, as are listed, for example, in the publication "Kosmetische Färbemittel" [Cosmetics Colorants] from the Farbstoff-kommission der Deutschen Forschungsgemeinschaft [Dyes Commission of the German Research Council], Verlag Chemie, Weinheim, 1984, pp. 81–106. These dyes are normally used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

EXAMPLES

TABLE 1

Standard emulsions - quantitative data in % by weight based on the final concentration -

| Standard emulsion | (I) | (II) |
|---|---|---|
| Ceteareth-20 | 2 | 2 |
| Cetearyl alcohol | 2 | 2 |
| Glyceryl stearate | 4 | 4 |
| Oil body | 20 | 20 |
| Octyl methoxycinnamate | — | 4 |
| Butyl methoxydibenzoylmethane | — | 4 |
| Glycerol | 5 | 5 |
| Carbomer | 0.2 | 0.2 |
| Water, preservative | ad 100 | |

A) Subjective Assessment of Skin Smoothness

A panel consisting of 5 experienced people tested formulations based on a standard emulsion (I) which comprised various oil body mixtures for their subjective feel on the skin. This was based on a scale between 1 (virtually no smoothing or rapid decrease in the feeling of smoothness) and 6 (rapid uniform feeling of smoothness). The figures in table 2 are average values. Examples 1 to 6 are according to the invention, and examples C1 to C9 serve for comparison.

A1: C8 Epo/n-octanol (oil component according to the invention)

B1: Dicaprylyl ether

B2: Cetearyl isononanoate

B3: Isopropyl myristate

B4: Dioctyl cyclohexane

B5: Almond oil

B6: Oleyl erucate

TABLE 2

Cosmetic formulations

| Example | Component 1 | Component 2 | Ratio | Skin smoothness |
|---|---|---|---|---|
| 1 | A1 | — | 100:00 | 5.7 |
| 2 | A1 | B1 | 50:50 | 5.4 |
| 3 | A1 | B2 | 60:40 | 5.5 |
| 4 | A1 | B3 | 40:60 | 5.8 |
| 5 | A1 | B4 | 50:50 | 5.4 |
| 6 | A1 | B5 | 80:20 | 5.2 |
| 7 | A1 | B6 | 80:20 | 5.3 |
| C1 | — | B1 | 0:100 | 3.0 |
| C2 | — | B2 | 0:100 | 3.2 |
| C3 | — | B3 | 0:100 | 2.0 |
| C4 | — | B4 | 0:100 | 2.4 |
| C5 | — | B5 | 0:100 | 1.3 |
| C6 | — | B6 | 0:100 | 1.5 |
| C7 | B1 | B2 | 50:50 | 3.2 |
| C8 | B3 | B6 | 80:20 | 2.9 |
| C9 | B4 | B5 | 80:20 | 2.2 |

Above an average value of 5.0, the feeling of smoothness on the skin is excellent, and below 5.0 the result is unsatisfactory.

B) Dissolving Capacity of Lipophilic Solids

Solubility of octyltriazone in:

| | |
|---|---|
| Dibutyl adipate | 10% |
| Dicaprylyl ether | 0% |
| Hexyl laurate | 0% |
| Cocoglycerides | 5% |
| Dioctyl malate | 10% |
| C12–15-alkyl benzoates | 10% |
| C12 Epo/methanol | 40% |
| C8 Epo/n-octanol | 30% |

C) Improvement in the Photostability

The photostability of the octyl methoxycinnamate/butyl-methoxydibenzoylmethane UV filter combination was tested in a standard emulsion (II). Here, the effect on the photostability of the oil component A1 according to the invention compared with the oils B1–B6 was determined according to the method published by Merck on the occasion of the APV seminar on Sep. 17–18, 1997 in Fulda. The results are summarized in table 3 below. Here, the photostability of the emulsion based on the oil component A1 according to the invention was set as 100% and compared.

TABLE 3

Cosmetic formulations

| Example | Component 1 | Component 2 | Ratio | Photo-stability |
|---|---|---|---|---|
| 1 | A1 | — | 100:00 | 100% |
| 2 | A1 | B1 | 50:50 | 89% |
| 3 | A1 | B2 | 60:40 | 92% |
| 4 | A1 | B3 | 40:60 | 82% |
| 5 | A1 | B4 | 50:50 | 89% |
| 6 | A1 | B5 | 80:20 | 94% |
| 7 | A1 | B6 | 80:20 | 96% |
| C1 | — | B1 | 0:100 | 55% |
| C2 | — | B2 | 0:100 | 63% |
| C3 | — | B3 | 0:100 | 42% |
| C4 | — | B4 | 0:100 | 39% |
| C5 | — | B5 | 0:100 | 45% |
| C6 | — | B6 | 0:100 | 66% |
| C7 | B1 | B2 | 50:50 | 60% |
| C8 | B3 | B6 | 80:20 | 54% |
| C9 | B4 | B5 | 80:20 | 40% |

TABLE 4

Sunscreen/care emulsions of the O/W type - quantitative data in % by weight based on the final concentration

| Component (INCI) | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| L = Lotion, C = cream | L | C | C | L | C | L | L | C | L | C | L | C | L | L | C | L | C | L | L | L | L | C |
| Polyglyceryl-2 Dipolyhydroxystearate (and) Lauryl Glucoside (and) Glycerin | | | | 3.5 | | 4 | 4 | | | | | 4 | 3 | 4 | | 3 | | 4 | | | | 2 |
| Ceteareth-20 | 2 | | | | | | | | | 2 | | | | | | | | | | 1 | | |
| Polysorbate 60 | | 1 | | | | | | | | | 1 | | | | | | | | | 1 | | |
| PEG-30 Stearate | | | 3 | | | | | | | | | | | | | | 3 | | | | | |
| PEG-20 Glyceryl Stearate | 1 | | | | | | | | | | | | | 2 | | | | | | | | |
| Trilaureth-4 Phosphate | | | | | | | | | 2 | | | | | | | | | | | 1 | | |
| Sodium Cetearyl Sulfate | | | | | 1 | | | 1 | | | | | 1 | .5 | | | | 1 | | | | |
| Potassium Cetyl Phosphate | | | 1 | | 1 | | | | | 1 | | 1 | | | | 1 | | | | | | |
| Sodium Stearate | | | | 1 | | 1 | | | | | | | | | 1 | | | | | | | 1 |
| Cetearyl Glucoside + Ceteayl Alcohol | | | | 5 | | 5 | | | | 4 | | 6 | | | | 5 | | | | | | 4 |
| Polyglyceryl-3 Methylglucose | | | | | | | 5 | | 3 | | 5 | | | | | | | | | 4 | | |

TABLE 4-continued

Sunscreen/care emulsions of the O/W type - quantitative data in % by weight based on the final concentration

| Component (INCI) | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| Distearate | | | | | | | | | | | | | | | | | | | | | | |
| Glyceryl Stearate | 4 | | 4 | 6 | | 4 | | | 6 | | | 3 | | 6 | 8 | 6 | 8 | | | | 4 | |
| Myristyl Alcohol | 1 | | | 1 | | | 2 | | | | 4 | | 2 | | | | | | 2 | | 1 | |
| Cetearyl Alcohol | 1 | 6 | | | 5 | 2 | | | | | | | | | 2 | | 3 | | | 1 | 1 | 6 |
| PVP/Hexadecene Copolymer | 1 | 1 | | | | | | | | | | | | | | | 2 | | | | | |
| Lanolin Alcohol | | | | | | .5 | .5 | | | | | | | | | | | | | | | |
| Lanolin | | | | | | 5 | | | | | | | | | | 4 | | | | | | |
| C12 Epo/Methanol | | 4 | 4 | | 8 | 4 | | 5 | 10 | | | 4 | | 4 | 8 | 6 | 6 | | | 4 | 4 | |
| C8 Epo/Octanol | 6 | | | 6 | | 2 | 5 | 5 | | 5 | 8 | | 10 | 4 | 2 | | | 10 | 8 | | | 5 |
| Myristyl Lactate | | | | | | | | | | | | 4 | | | | | | | | | | |
| Propylene Glycol | | | | 5 | | | | | | 6 | | | | | | 5 | | | 5 | | | |
| Dicaprylate/Dicaprate Cocoglycerides | 5 | | | | | 6 | | 6 | | | | 5 | | 5 | | | | 7 | | 3 | 10 | 8 |
| C12/15 Alkyl Benzoate | | | 3 | | | | | | 8 | | | | | | 5 | | | 3 | 3 | | | |
| Dicaprylyl Carbonate | | 2 | | | | 4 | | | | | | | | | | | | | | | | |
| Dicaprylyl Ether | | | 3 | | | | | | 2 | 3 | | | | | 2 | | 2 | | | | | |
| Cyclomethicone | 4 | | 1 | 5 | | | | | | | 2 | | 2 | | 1 | | | | | | | |
| Cetyl Dimethicone | | 1 | | 2 | | | | | | | | 1 | 1 | | | | | | | | | 3 |
| Dimethicone | | 2 | | | 4 | | | | | | | | | | 1 | | | | | | | |
| Octyl Stearate | | | 2 | 2 | | 4 | | | | 7 | | 2 | | | | | | | | | | |
| Oleyl Erucate | | | | 3 | 2 | | | | 5 | | | 2 | | | | | | | | 1 | | |
| Mineral Oil | | | | | 9 | | | | | | | | | | 10 | | | | | | | |
| Butyl Adipate | | 1 | | | | | | | | 2 | | | | | | 5 | | 4 | | | | 3 |
| Octyldodecanol | | | | | | | | | | | | | 3 | 5 | | | | | | | | |
| Hexyldecanol + Hexyldecyllaurate | | 5 | | | | | | | 5 | | | | | | | | | | | 2 | | |
| Almond Oil | | 2 | | | | 1 | | | | | | | | | | | 2 | 3 | | | | 2 |
| Panthenol | | | | | | | | | | | | 1 | | | | | | | | | | |
| Bisabolol | | | | | | | | | | | | 0.2 | | | | | | | | | | |
| Tocopherol/Tocopheryl Acetate | | | | | | | | | | | | 1 | | | | | | | | | | |
| Chitosan | | | | | | | | | 0.2 | | | | | 0.2 | | | | | 0.2 | | | |
| Phenylbenzimidazole Sulfonic Acid (Sodium Salt) | 2 | | 2.2 | 3 | 3 | | | | | | | | | | | | | | | | | |
| Octocrylene | 3 | 5 | | | | | | | 4 | | | | | | | | | | | | | |
| Benzophenone-3 | | | | 4 | 3 | | | | | | | | | | | | | | | | | |
| 4-Methylbenzylidene Camphor | 2 | | 3 | 3 | | 2 | 2 | | | | | | | | | | | | | | | |
| Octyl Salicylate | | | | | | | | | 10 | 7 | | | | | | | | | | | | |
| Isoamyl p-Methoxycinnamate | | 7.5 | 6 | 6 | | | | | | | | | | | | | | | | | | |
| Octyl Methoxycinnamate | | | | | | 7.5 | 4 | 5 | | | | | | | | | | | | | | |
| Octyl Triazone | 2 | | | | 2.5 | | 3 | | | | | | | | | | | | | | | |
| Butyl Methoxy-dibenzoylmethane | | 1 | 1 | | | 2 | 2 | 2 | | | | | | | | | | | | | | |
| Zinc Oxide (micronized) | 10 | | | | | 10 | | | | 6 | | | | | | | | | | | | |
| Titanium Dioxide (surface-treated) | | | 10 | 6 | 5 | | 3 | | | | | | | | | | | | | | | |
| Magnesium Aluminum Silicates | | | 1 | | | | | | 1 | | | | | | | | | | | 1 | | |
| Xanthan Gum | | | .5 | | | | | | .5 | | | | | .2 | | | | | | .5 | | |
| Carbomer | | .5 | | | .2 | .2 | | .5 | | | .3 | .2 | | .3 | .2 | .3 | .5 | .2 | .1 | | .3 | |
| Acrylates/C10–30 Alkyl Acrylate Crosspolymer | | | | .2 | | | | | | | | | | | | | | | | .2 | | |
| Ethanol | | | | | | | | | | 10 | | | 5 | | 8 | | | | | | | 10 |
| Butylene Glycol | | 2 | | 4 | 3 | | 2 | 5 | 2 | | | 5 | | 2 | 3 | 3 | | | | 8 | | |
| Glycerol | 5 | 5 | 5 | | 3 | 3 | 2 | | 4 | 5 | 3 | 2 | 4 | 3 | 3 | | 7 | 5 | 3 | 5 | | 5 |
| Water, preservatives, NaOH (pH 5–6) | | | | | | | | | | ad 100 | | | | | | | | | | | | |

Sunscreen emulsions (1–10); care emulsions (11–22)

TABLE 5

Sunscreen/care emulsions of the W/O type - quantative data in % by weight based on the final concentration

| Component (INCI) | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|
| L = lotion, C = cream | C | L | C | L | C | L | L | L | C | C | C | L | C | L | L | C | L | L | L | L | C | C |
| Polyglyceryl-2 Dipolyhydroxystearate | 4 | 2 |   | 3 | 3 |   |   | 2 | 1 |   |   | 3 |   | 5 |   |   | 3 |   | 4 |   |   | 1 |
| Glyceryl Oleate |   |   | 2 |   |   |   |   |   |   |   |   |   | 1 |   |   |   |   |   |   |   |   | 3 |
| Polyglyceryl-3 Diisostearate |   |   | 4 |   | 3 |   |   |   | 4 | 1 | 3 |   |   |   |   | 4 |   |   | 1 |   | 3 |   |
| Ceryl Dimethicone Copolyol |   | 1 |   |   |   |   | 4 |   |   |   |   |   |   |   | 1 |   |   |   |   |   | 2 |   |
| Methyl Glucose Dioleate | 2 |   |   |   |   |   |   |   |   |   | 3 |   |   |   | 3 |   |   |   |   | 2 |   |   |
| PEG-30 Dipolyhydroxystearate |   |   |   |   |   |   |   |   | 1 |   |   | 2 |   |   |   |   |   | 4 |   |   |   | 1 |
| Diisostearoyl Polyglyceryl-3 Diisostearate |   |   |   |   |   | 4 |   | 2 |   |   |   |   | 3 |   |   |   |   | 4 |   |   |   |   |
| Sorbitan Sesquioleate |   |   |   | 2 |   |   |   |   |   |   |   |   |   |   |   |   | 3 |   |   |   |   |   |
| Dicocoyl Pentaerythrityl Distearyl Citrate |   |   |   | 2 |   |   |   |   |   |   |   |   |   |   |   | 4 |   |   |   |   |   |   |
| PEG-7 Hydrogenated Castor Oil |   |   |   |   |   |   |   |   |   | 4 |   |   |   |   |   |   |   |   |   | 4 |   |   |
| Zinc Stearate | 2 | 1 |   | 1 | 1 |   |   | 1 | 1 | 1 |   |   | 2 | 2 | 1 | 1 | 1 |   | 1 | 1 |   | 1 |
| Microcrystalline Wax |   |   | 5 |   |   | 2 |   |   |   |   | 5 |   |   |   |   | 4 |   | 1 |   |   | 4 |   |
| Beeswax | 4 | 1 |   | 1 |   |   |   | 5 | 4 | 7 |   |   | 4 |   | 2 |   | 2 | 1 | 1 | 2 |   | 5 |
| Cetearyl Glucoside |   |   |   |   | 1 |   |   |   |   |   |   |   |   | .5 |   |   |   |   |   |   |   |   |
| Isostearic Acid |   |   | 1 |   | 1 | 1 | 1 |   |   |   |   |   |   |   |   |   |   |   | 1 |   |   |   |
| PVP/Hexadecene Copolymer |   |   |   |   | 1 |   |   |   |   |   |   |   |   |   |   |   |   | 1 |   |   |   |   |
| Lanolin Alcohol | 1 |   |   |   |   |   |   |   |   | 1 |   |   |   |   |   |   |   |   |   |   |   |   |
| Lanolin |   |   | 5 |   |   |   |   |   |   | 4 |   |   | 7 | 3 |   |   |   |   |   |   |   |   |
| C12 Epo/Methanol (oil component according to the invention) | 5 | 8 | 3 | 4 |   |   | 8 | 5 |   | 8 |   |   | 10 |   |   | 10 |   | 7 | 3 | 4 | 10 | 2 |
| C 8 Epo/Octanol (oil component according to the invention) |   |   | 4 |   | 6 | 8 | 5 |   | 5 | 4 |   | 12 |   | 8 | 8 |   | 8 |   | 7 |   |   | 5 |
| Myristyl Lactate |   |   | 3 |   |   |   |   |   | 1 |   |   |   | 2 |   |   |   |   |   |   |   |   |   |
| Propylene Glycol Dicaprylate/Dicaprate |   |   |   |   | 3 |   |   | 4 |   |   |   |   |   |   |   |   |   |   |   |   |   |   |
| Cocoglycerides | 6 |   |   | 3 | 6 |   |   |   |   | 8 | 4 |   | 3 |   |   | 5 |   |   |   | 5 | 4 |   |
| C12/15 Alkyl Benzoate |   |   |   | 5 |   |   | 5 |   |   |   |   |   |   |   | 5 |   |   | 7 |   |   |   |   |
| Dicaprylyl Carbonate |   | 4 |   |   |   | 2 |   |   |   |   | 5 | 3 |   | 2 |   |   |   | 3 |   |   |   |   |
| Dicaprylyl Ether | 3 |   |   |   | 4 |   | 5 |   | 4 | 2 |   |   | 3 |   | 2 |   |   | 3 |   |   |   |   |
| Cyclomethicone |   | 3 |   |   |   |   | 2 |   |   |   |   |   | 4 |   | 2 |   |   |   |   |   |   |   |
| Cetyl Dimethicone |   |   | 1 |   | 2 |   |   |   |   |   |   |   |   |   | 1 |   |   |   |   |   |   |   |
| Dimethicone |   |   |   | 4 |   |   |   | 3 |   |   |   |   |   |   | 1 |   |   |   | 4 |   |   |   |
| Octyl Stearate |   |   |   |   |   |   |   |   |   | 2 |   |   |   |   |   |   |   |   |   |   |   | 10 |
| Oleyl Erucate |   |   | 4 |   |   | 2 |   |   |   |   |   |   |   |   | 3 |   |   |   |   |   |   |   |
| Diocryl Malate |   |   |   | 2 |   |   |   | 2 |   | 6 |   |   |   |   | 1 |   |   |   |   | 5 | 4 |   |
| Mineral Oil |   |   |   | 4 |   |   |   |   |   |   |   |   |   |   |   |   |   | 9 |   |   |   |   |
| Butyl Adipate |   |   |   | 2 | 4 |   |   |   |   | 3 |   |   |   |   |   | 3 | 3 |   | 2 | 2 |   |   |
| Ocryldodecanol |   |   | 3 |   |   |   | 8 |   |   |   |   |   |   |   | 2 |   |   |   |   | 5 |   |   |
| Hexyldecanol (and) Hexyldecyllaurate |   | 11 |   |   | 4 |   |   | 9 |   |   |   |   |   |   |   |   |   |   | 6 |   |   | 3 |
| Almond Oil |   |   |   | 1 |   | 5 |   |   |   |   |   |   |   | 2 |   |   |   |   |   |   |   |   |
| Panthenol |   |   |   |   |   |   |   |   |   |   | 1.0 |   |   |   |   |   |   |   |   |   |   |   |
| Bisabolol |   |   |   |   |   |   |   |   |   |   | 0.2 |   |   |   |   |   |   |   |   |   |   |   |
| Tocopherol/Tocopheryl Acetate |   |   |   |   |   |   |   |   |   |   | 1.0 |   |   |   |   |   |   |   |   |   |   |   |
| Chitosan | 0.2 |   |   |   |   |   |   |   |   |   |   |   |   |   |   |   |   | 0.3 |   |   |   |   |
| Phenylbenzimidazole Sulfonic Acid (Sodium Salt) |   | 1 |   | 3 |   |   |   |   |   |   |   |   |   |   |   |   |   |   |   |   |   |   |
| Octocrylene | 5 |   |   |   | 4 |   |   |   | 6 |   |   |   |   |   |   |   |   |   |   |   |   |   |
| Benzophenone-3 |   |   | 2 | 4 |   |   | 2 |   |   |   |   |   |   |   |   |   |   |   |   |   |   |   |
| 4-Methylbenzylidene Camphor | 3 | 3 |   |   |   |   |   | 4 |   | 3 |   |   |   |   |   |   |   |   |   |   |   |   |
| Octyl Salicylate |   |   |   |   |   |   |   |   |   |   |   |   |   |   |   |   |   |   |   |   |   |   |
| Isoamyl p-Methoxycinnamate |   | 7.5 |   |   |   |   |   |   | 5 |   |   |   |   |   |   |   |   |   |   |   |   |   |
| Octyl Methoxycinnamate |   |   | 6 | 6 |   | 7.5 | 7.5 |   |   |   |   |   |   |   |   |   |   |   |   |   |   |   |
| Octyl Triazone | 2 |   |   | 2.5 |   |   |   | 1 | 3 |   |   |   |   |   |   |   |   |   |   |   |   |   |
| Butyl Methoxydibenzoylmethane | 1 | 2 |   |   |   |   |   | 1 | 2 | 2 |   |   |   |   |   |   |   |   |   |   |   |   |
| Zinc Oxide (micronized) |   |   |   | 5 | 6 |   |   |   |   |   |   |   |   |   |   |   |   |   |   |   |   |   |
| Titanium Dioxide (surface-treated) |   |   | 10 |   |   |   | 4 |   |   |   |   |   |   |   |   |   |   |   |   |   |   |   |
| Ethanol |   |   |   |   |   |   |   |   |   | 8 |   |   |   |   | 8 |   | 10 |   |   |   |   |   |
| Butylene Glycol |   |   | 6 | 3 |   | 2 | 5 |   |   |   |   | 5 |   |   | 3 | 3 |   |   |   | 8 | 2 | 1 |
| Glycerol | 5 | 3 | 3 |   | 5 | 3 |   | 4 | 10 | 4 | 3 |   | 4 | 6 | 3 |   | 4 | 5 | 5 |   | 3 | 5 |
| Water, preservatives |   |   |   |   |   |   |   |   |   |   | ad 100 |   |   |   |   |   |   |   |   |   |   |   |

Sunscreen emulsions (23–32); care emulsions (33–34)

What is claimed is:

1. A method of preparing a cosmetic or pharmaceutical composition, said method comprising:
   (a) providing a hydroxyether prepared by ring opening an olefin epoxide having from 6 to 18 carbon atoms with a component selected from the group consisting of an alcohol having from 1 to 18 carbon atoms, a polyol having from 2 to 18 carbon atoms and from 2 to 10 hydroxyl groups, and mixtures thereof;
   (b) providing a lipophilic solid; and
   (c) combining the hydroxyether and the lipophilic solid.

2. The method according to claim 1, wherein the lipophilic solid comprises a component selected from the group consisting of UV light protection filters, waxes, fats, stabilizers, pearlescent waxes, polymers and partial glycerides.

3. The method according to claim 1, wherein the hydroxyether and the lipophilic solid are combined such that the hydroxyether is present in an amount of from 1 to 60% by weight, and the lipophilic solid is present in an amount of from 0.1 to 30% by weight, based on the cosmetic or pharmaceutical composition.

4. A cosmetic or pharmaceutical composition comprising:
   (a) from 1 to 60% by weight of a hydroxyether prepared by ring opening an olefin epoxide having from 6 to 18 carbon atoms with a component selected from the group consisting of an alcohol having from 1 to 18 carbon atoms, a polyol having from 2 to 18 carbon atoms and from 2 to 10 hydroxyl groups, and mixtures thereof; and
   (b) from 0.1 to 30% by weight of a lipophilic solid, all weight percents based upon the total composition.

5. The cosmetic or pharmaceutical composition according to claim 4, wherein the lipophilic solid comprises a component selected from the group consisting of UV light protection filters, waxes, fats, stabilizers, pearlescent waxes, polymers and partial glycerides.

6. The cosmetic or pharmaceutical composition according to claim 4, wherein the olefin epoxide is selected from a group consisting of α-hexene epoxide. α-octene epoxide, α-decene epoxide, α-dodecene epoxide. α-hexadecene epoxide, α-octadecene epoxide, i-hexene epoxide, i-octene epoxide, i-decene epoxide, i-dodecene epoxide, i-hexadecene epoxide and i-octadecene epoxide.

7. The cosmetic or pharmaceutical composition according to claim 4, wherein the epoxide is selected from a group consisting of octene, decene and dodecene epoxides.

8. The cosmetic or pharmaceutical composition according to claim 4, wherein the alcohol is selected from a group consisting of lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol and linolenyl alcohol.

9. The cosmetic or pharmaceutical composition according to claim 4, wherein the alcohol is selected from branched and cyclic alcohols having 1 to 8 carbon atoms.

10. The cosmetic or pharmaceutical composition according to claim 4, wherein the polyol has 4 to 10 carbon atoms.

11. The method according to claim 1, wherein the olefin epoxide is selected from a group consisting of α-hexene epoxide, α-octene epoxide, α-decene epoxide, α-dodecene epoxide, α-hexadecene epoxide, α-octadecene epoxide, i-hexene epoxide, i-octene epoxide, i-decene epoxide, i-dodecene epoxide, i-hexadecene epoxide and/or i-ootadecene epoxide.

12. The method according to claim 1, wherein the epoxide is selected from a group consisting of octene, decene and dodecene epoxides.

13. The method according to claim 1, wherein the alcohol is selected from a group consisting of lauryl alcohol, coconut fatty alcohol, myristyl alcohol, cetyl alcohol, cetearyl alcohol, stearyl alcohol, isostearyl alcohol, oleyl alcohol, elaidyl alcohol, petroselinyl alcohol, linolyl alcohol and/or linolenyl alcohol.

14. The method according to claim 1, wherein the alcohol is selected from branched and cyclic alcohols having 1 to 8 carbon atoms.

15. The cosmetic or pharmaceutical composition according to claim 1, wherein the polyol has 4 to 10 carbon atoms.

* * * * *